United States Patent [19]
Kitaoka

[11] Patent Number: 6,129,840
[45] Date of Patent: Oct. 10, 2000

[54] LIQUID CHROMATOGRAPH

[75] Inventor: Mitsuo Kitaoka, Kyoto, Japan

[73] Assignee: Shimadzu Corporation, Kyoto, Japan

[21] Appl. No.: 09/334,913

[22] Filed: Jun. 17, 1999

[30] Foreign Application Priority Data

Jun. 19, 1998 [JP] Japan .................................. 10-172563

[51] Int. Cl.[7] .................................................. B01D 15/08
[52] U.S. Cl. ........................ 210/198.2; 210/101; 210/656
[58] Field of Search .................................... 210/635, 656, 210/659, 198.2, 101, 143; 73/61.55, 61.56

[56] References Cited

U.S. PATENT DOCUMENTS

| | | | |
|---|---|---|---|
| 5,100,557 | 3/1992 | Nogami et al. ........................ | 210/656 |
| 5,131,998 | 7/1992 | Jorgenson .............................. | 210/198.2 |
| 5,158,675 | 10/1992 | Allington .............................. | 210/198.2 |
| 5,180,487 | 1/1993 | Saito ..................................... | 210/198.2 |
| 5,567,307 | 10/1996 | Karmarkar ............................ | 210/198.2 |
| 5,674,388 | 10/1997 | Anahara ................................ | 210/198.2 |
| 5,738,783 | 4/1998 | Shirota ................................. | 210/198.2 |
| 5,852,231 | 12/1998 | Kaji ...................................... | 210/198.2 |
| 5,935,443 | 8/1999 | Anderson ............................. | 210/198.2 |
| 5,958,227 | 9/1999 | Uematsu .............................. | 210/198.2 |

OTHER PUBLICATIONS

United Kingdom Search Report of Sept. 15, 1999.

*Primary Examiner*—Ernest G. Therkorn
*Attorney, Agent, or Firm*—Armstrong, Westerman, Hattori, McLeland & Naughton

[57] ABSTRACT

When a signal for filling up with or substituting a mobile phase is externally transmitted to a control part, the control part switches a valve for connecting a channel from a pump part to a sampling needle through a sampling loop and moves the sampling needle toward a drain port. Thus, a channel is formed through a mobile phase container→a pump→the valve→the sampling loop→the sampling needle→the drain port. In this channel state, the control part drives the pump at a high speed for substituting the channel connecting the pump and the sampling needle by a desired mobile phase.

5 Claims, 6 Drawing Sheets

(A) Ready (B) De-press (C) Load (D) INJ / Purge in (E) Purge out (F) Auto Drain

LIQUID CHROMATOGRAPH

BACKGROUND OF THE INVENTION

1. Field of the Invention

The present invention relates to a liquid chromatograph such as a high-performance liquid chromatograph (HPLC) separating and analyzing various compounds within a sample.

2. Description of the Prior Art

FIG. 1 is a schematic channel block diagram showing a conventional HPLC, which is formed by a column 5 separating a sample, a pump part 1 feeding a mobile phase to the column 5, an auto injector 3 collecting the sample from a sampling needle 39 to a sampling loop 27 and introducing the collected sample into a mobile phase channel upstream the column 5 by switching a channel switching valve 29, a detection part 7 detecting the sample separated in the column 5 and a control part 41 controlling the operations of the pump part 1 and the auto injector 3.

The pump part 1 has a double plunger reciprocating feed pump 9. A suction side of a primary pump head 11 of the pump 9 is connected to a mobile phase container 15 storing the mobile phase through a check valve 13a, while a discharge side thereof is connected to a suction side of a secondary pump head 17 through a check valve 13b. A discharge side of the secondary pump head 17 is connected to the auto injector 3 through a drain valve 19 and a line filter 21. A pressure sensor 23 is provided on a channel between the secondary pump head 17 and the drain valve 19. The discharge side of the secondary pump head 17 can be switched and connected to the auto injector 3 or a drain by manually switching a lever 25 of the drain valve 19.

The auto injector 3 has a two-position six-port valve 29 switching and connecting a channel from the pump part 1 to the sampling loop 27 or the column 5. The sampling loop 27 is connected with the sampling needle 39 moving between an injection port 35 and a sample container 37 for sucking the sample from the sample container 37 and discharging the same in the injection port 35. The injection port 35 is connected to the column 5 by switching the valve 29. A measuring syringe 33 is connected to one port of the valve 29 through a three-way valve 31, to be connected to the sampling loop 27 by switching the valve 29.

The detection part 7 detecting the sample separated in the column 5 is connected downstream the column 5.

Channels between the injection port 35 and the valve 29, between the valve 29 and the column 5 and between the column 5 and the detection part 7 are formed by thin pipes for preventing the sample from dilution.

When filling up the overall channels with the mobile phase or substituting the mobile phase in this prior art, it takes remarkable time to substitute the mobile phase in the pump 9 having a relatively large volume if feeding the mobile phase at an ordinary low speed. However, if feeding the mobile phase at a high speed, pressure increases due to the thin pipes subsequent to the injection port 35 including the column 5. Therefore, the mobile phase cannot be fed to the channels subsequent to the injection port 35 at a high speed. In this regard, the pump 9 is driven at a high speed after switching the drain valve 19 to the drain side in the pump part 1 for introducing the mobile phase into the pump 9.

At this time, the lever 25 of the drain valve 19 is first manually moved to connect the discharge side of the secondary pump head 17 to the drain. Then, the pump 9 is driven at a high speed to discharge the mobile phase from the drain through the drain valve 19. After the primary and secondary pump heads 11 and 17 are filled up with a new mobile phase, the pump 9 is returned to an ordinary speed and the lever 25 of the drain valve 19 is manually switched to connect the discharge side of the secondary pump head 17 to the auto injector 3, thereby feeding the new mobile phase to the overall channels.

It is troublesome for an operator to manually open/close the drain valve 19 for substituting the mobile phase and automatization is awaited. However, in order to automatically open/close the drain valve 19, a high-torque motor is required since high pressure is applied to the drain valve 19, leading to a high cost for the apparatus.

SUMMARY OF THE INVENTION

The objective of the present invention is to automatize introduction or substitution of a mobile phase in a liquid chromatograph without increasing the cost.

A liquid chromatograph according to the present invention comprises a column separating a sample, a feed part feeding a mobile phase to the column, a sample introduction part collecting the sample from a sampling needle into a sampling loop and introducing the collected sample into a mobile phase channel upstream the column by switching a channel switching valve, a detection part detecting the sample separated in the column and a control part controlling the operations of the feed part and the sample introduction part. The liquid chromatograph further comprises a drain port discharging a liquid discharged from the sampling needle outward, switches a channel switching valve by the control part for connecting the feed part to a channel connecting the sampling loop with the sampling needle while locating the sampling needle on the drain port, and switches the feed part by control part to high-speed driving.

When a signal for filling up a channel with a mobile phase or a signal for exchanging the mobile phase is externally transmitted to the control part, the control part controls the feed part and the sample introduction part for switching the channel switching valve to connect the feed part to the sampling needle, moving the sampling needle from an injection port to the drain port, and increasing the flow rate of the feed part. The mobile phase is discharged from the feed part of the apparatus through the channel switching valve, the sampling loop, the sampling needle and the drain port at a high speed so that the channel is substituted by a desired mobile phase. Thereafter, the sampling needle is returned to the injection port and the flow rate of the pump is returned to a low speed for feeding the mobile phase, thereby completing filling up or liquid substitution of the overall channel with the mobile phase.

Consequently, not only a motor for a drain valve but also the drain valve itself is unnecessary in the liquid chromatograph according to the present invention, and filling up with or substitution of the mobile phase can be automatized without increasing the cost for the apparatus.

The foregoing along with other objectives, features, aspects and advantages of the present invention will become more apparent from the following detailed description of the present invention when taken in conjunction with the accompanying drawings.

DESCRIPTION OF THE PREFERRED EMBODIMENTS

Figure 1:
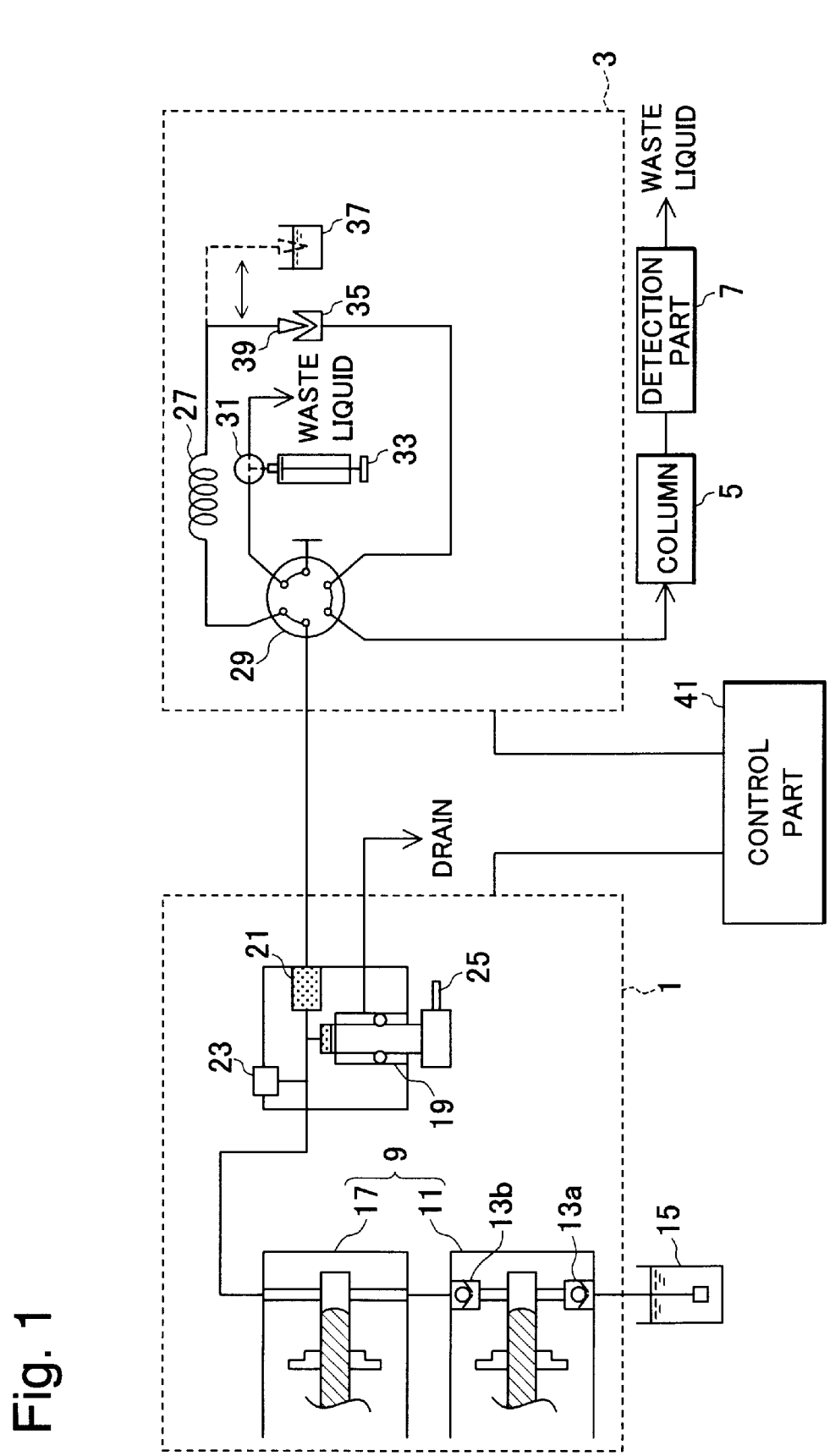
FIG. 1 is a schematic channel block diagram showing a conventional HPLC.
Figure 2:
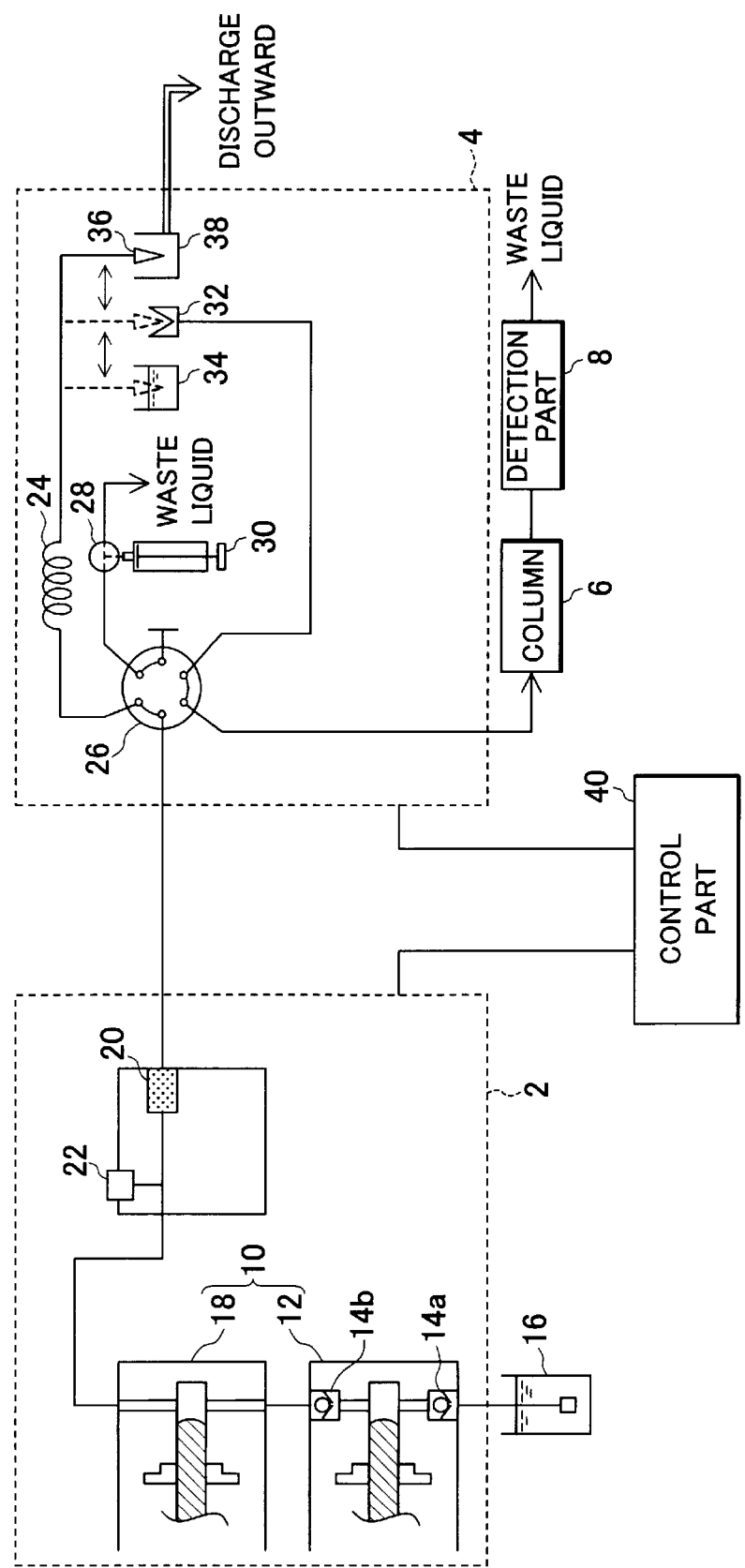
FIG. 2 is a schematic channel block diagram showing an embodiment of the present invention.

FIG. 2 is a schematic channel block diagram showing an embodiment of the present invention.

This embodiment comprises a pump part (feed part) 2 feeding a mobile phase, an auto injector (sample introduction part) 4 introducing a sample into a channel, a column 6 separating the sample and a detection part 8 sequentially detecting the separated sample.

The pump part 2 has a double plunger reciprocating feed pump 10. A suction side of a primary pump head 12 of the pump 10 is connected to a mobile phase container 16 storing a mobile phase through a check valve 14a, while a discharge side thereof is connected to a suction side of a secondary pump head 18 through a check valve 14b. A discharge side of the secondary pump head 18 is connected to the auto injector 4 through a line filter 20 removing foreign matter mixed into the mobile phase. A pressure sensor 22 is provided on a channel between the secondary pump head 18 and the line filter 20.

The auto injector 4 has a two-position six-port valve 26 switching and connecting a channel from the pump part 2 to a sampling loop 24 or the column 6. The sampling loop 24 is connected with a sampling needle 36 moving between an injection port 32 and a sample container 34 for sucking a sample from the sample container 34 and discharging the same in the injection port 32. A drain port 38 discharging a liquid outward is provided in the vicinity of the injection port 32, and the sampling needle 36 can move also toward the drain port 38 for discharging a waste liquid outward through the drain port 38. The injection port 32 is connected to the column 6 by switching the valve 26. A measuring syringe 30 is connected to one port of the valve 26 through a three-way valve 28. This measuring syringe 30 is connected to the sampling loop 24 by switching the valve 26.

The detection part 8 detecting the sample separated in the column 6 is connected downstream the column 6.

Channels between the injection port 32 and the valve 26, between the valve 26 and the column 6 and between the column 6 and the detection part 8 are formed by thin pipes, for preventing the sample from dilution.

A control part 40 is provided for controlling the operations of the pump part 2 and the auto injector 4. In addition to controls of sample introduction and analysis, the control part 40 also controls operations of switching the channel switching valve 26 for connecting the pump part 2 to the sampling needle 36 through the sampling loop 24, of connecting the sampling needle 36 to the drain port 38, and of switching the pump 2 to high-speed driving.

Operations in analysis in this embodiment shall now be described. The control part 40 connects the channel from the pump part 2 to the column 6 through the valve 26 for feeding a mobile phase to the column 6, while connecting the measuring syringe 30 to the sampling loop 24. The control part 40 also moves the sampling needle 36 toward the sample container 34, and sucks the sample into the sampling loop 24 through the measuring syringe 30.

Thereafter the control part 40 moves the sampling needle 36 toward the injection port 32, and switches the valve 26 to the state shown in FIG. 2.

Thus, the mobile phase passes through the sampling loop 24 and flows from a part coupling the sampling needle 36 and the injection port 32 to the column 6, while the sample collected by the sampling loop 24 is injected into and separated in the column 6 and detected by the detection part 8.

Operations for filling up the channel with the mobile phase or substituting the mobile phase shall now be described.

When a signal for filling up with or substituting the mobile phase is externally transmitted to the control part 40, the control part 40 switches the valve 26 for connecting the channel from the pump part 2 to the sampling needle 36 through the sampling loop 24, and moves the sampling needle 36 toward the drain port 38. Thus, a channel is formed through the mobile phase container 16→the pump 10→the switching valve 26→the sampling loop 24→the sampling needle 36→the drain port 38. In this channel state, the control part 40 drives the pump 10 at a high speed for feeding the mobile phase at a high speed. By driving the pump 10 for a prescribed time, a desired mobile phase is introduced into the channel connecting the pump 10 with the sampling needle 36. A mobile phase discharged from the sampling needle 36 during the high-speed driving of the pump 10 is discharged outward through the drain port 38.

After a lapse of the prescribed time, the control part 40 returns the sampling needle 36 to the injection port 32, returns the pump 10 to an ordinary driving speed for feeding the mobile phase at a low speed, and introduces the mobile phase into the channels between the injection port 32 and the valve 26, between the valve 26 and the column 6 and between the column 6 and the detection part 8.

While detailed description of the operation for switching the valve 26 is omitted, the valve 26 is properly switched inclusive of the movement of the sampling needle 36.

According to the present invention, not only a motor for a drain valve but also the drain valve itself is unnecessary. Consequently, filling up with or substitution of the mobile phase can be automatized without increasing the cost for the apparatus.

Figure 3:
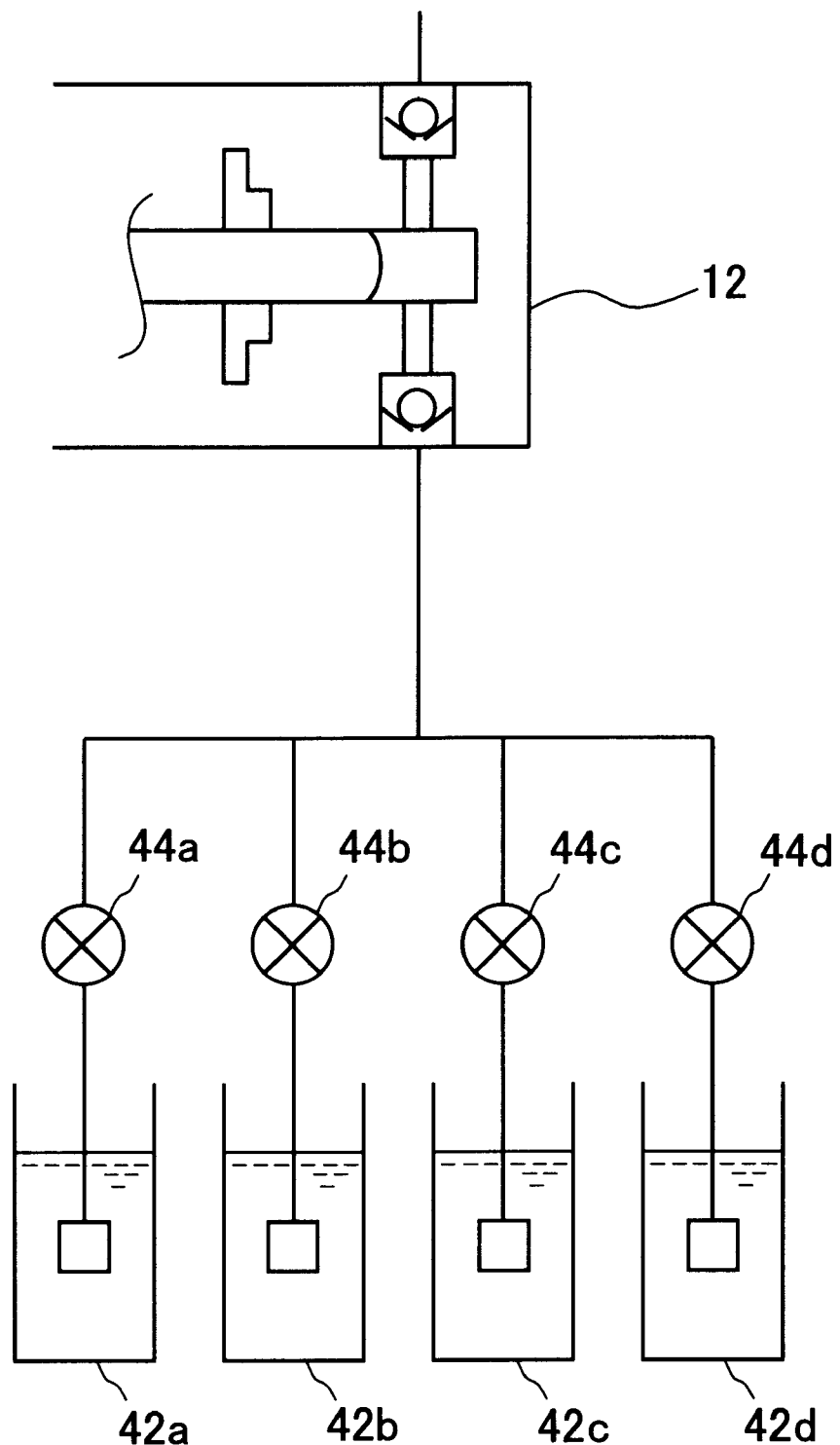
FIG. 3 is a schematic channel block diagram showing a mobile phase feed part of another embodiment.

FIG. 3 is a schematic block diagram showing a part of another embodiment of the present invention.

Mobile phase containers 42a, 42b and 42c storing mobile phases respectively and a cleaning solution container 42d storing a cleaning solution are connected to a suction side of a primary pump head of a pump part through electromagnetic valves 44a, 44b, 44c and 44d respectively.

The mobile phases or the cleaning solution can be selected by controlling opening/closing of the electromagnetic valves 44a, 44b, 44c and 44d, whereby the mobile phases can be selected and substituted only by a button operation and a channel cleaning step after analysis can be automatized.

Figure 4:
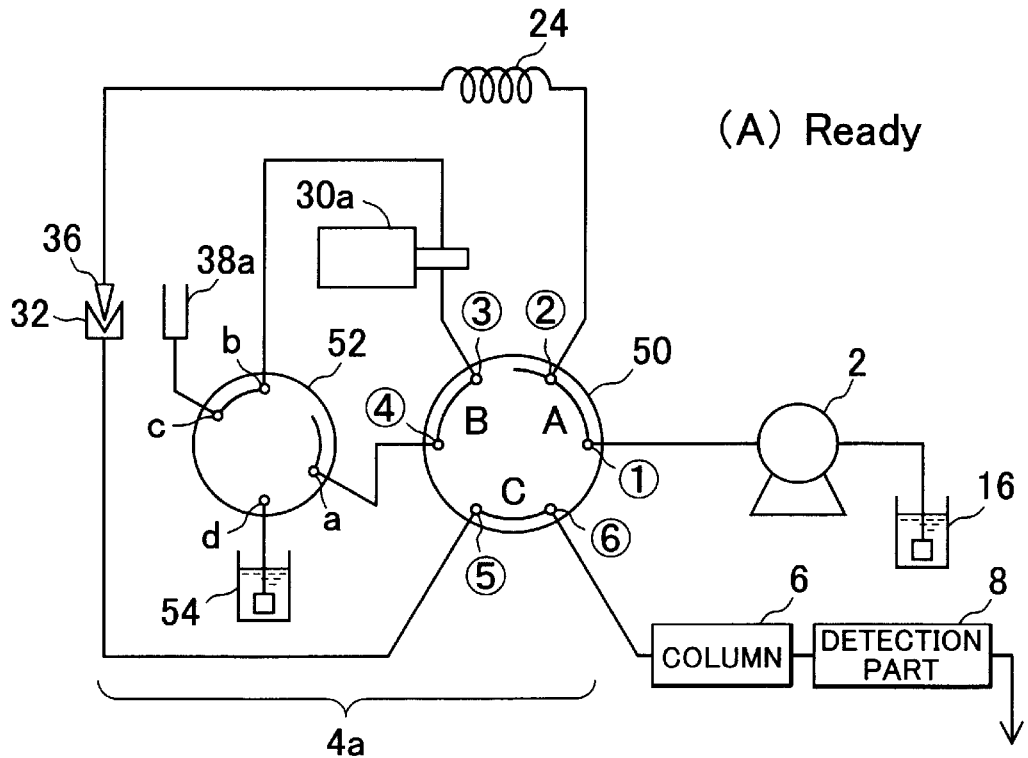
FIG. 4 is a schematic channel block diagram showing still another embodiment in a Ready position.

FIG. 4 shows still another embodiment of the present invention. An auto sampler 4a of a sample introduction part corresponding to the auto injector 4 in the embodiment shown in FIG. 2 has a high pressure valve 50 and a low pressure valve 52 for switching channels. The high pressure valve 50 has six ports $\hat{1}$ to $\hat{6}$ provided on a stator and three channel grooves A, B and C provided on a rotor for switching connection between these ports. The channel groove A is employed for switching and connecting the port $\hat{1}$ to the port $\hat{2}$ or $\hat{6}$, the channel groove B is employed for switching and connecting the port $\hat{4}$ to the port $\hat{3}$ or $\hat{5}$, and the channel groove C is employed for switching and connecting the port $\hat{5}$ to the port $\hat{4}$ or $\hat{6}$.

The channel groove A is longer than the distance between the ports $\hat{1}$ and $\hat{2}$ or between the ports $\hat{1}$ and $\hat{6}$. In other words, the channel groove A partially extends beyond an angle of rotation of 60°. Thus, not only the channel groove A connects the port $\hat{1}$ to the port $\hat{2}$ or $\hat{6}$ but such a state that the channel grooves B and C connect no ports can be taken as shown in an Auto Drain position of FIG. 9 described later. The high-pressure valve 50 is a three-position valve.

Figure 7:
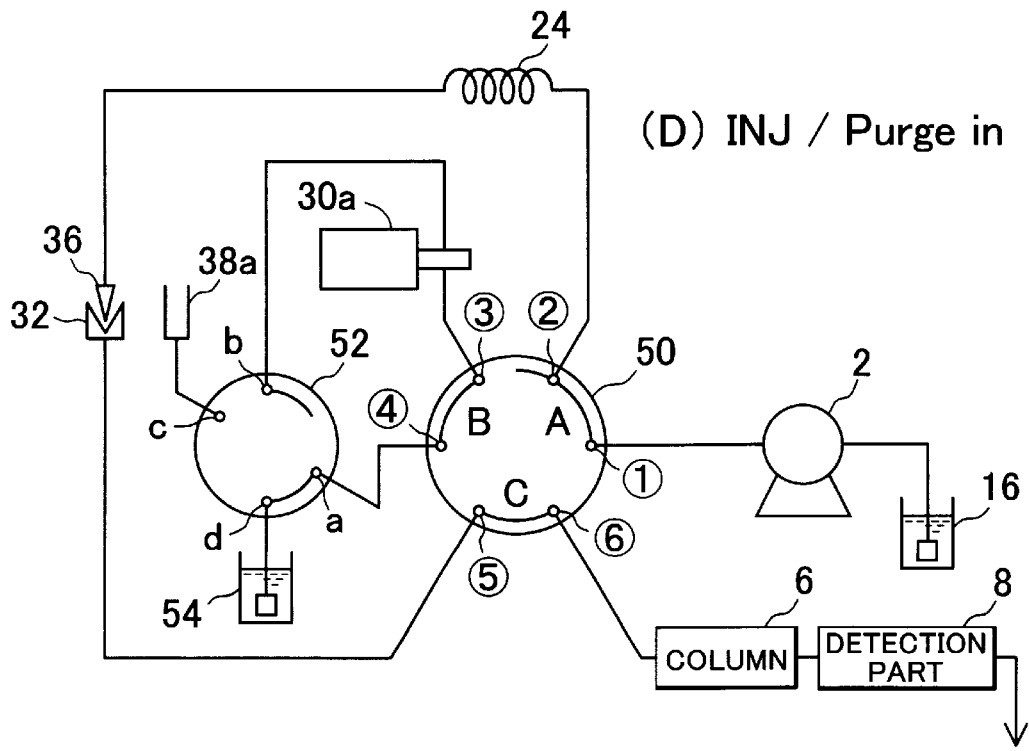
FIG. 7 is a schematic channel block diagram showing the embodiment in an INJ/Purge in position.
Figure 9:
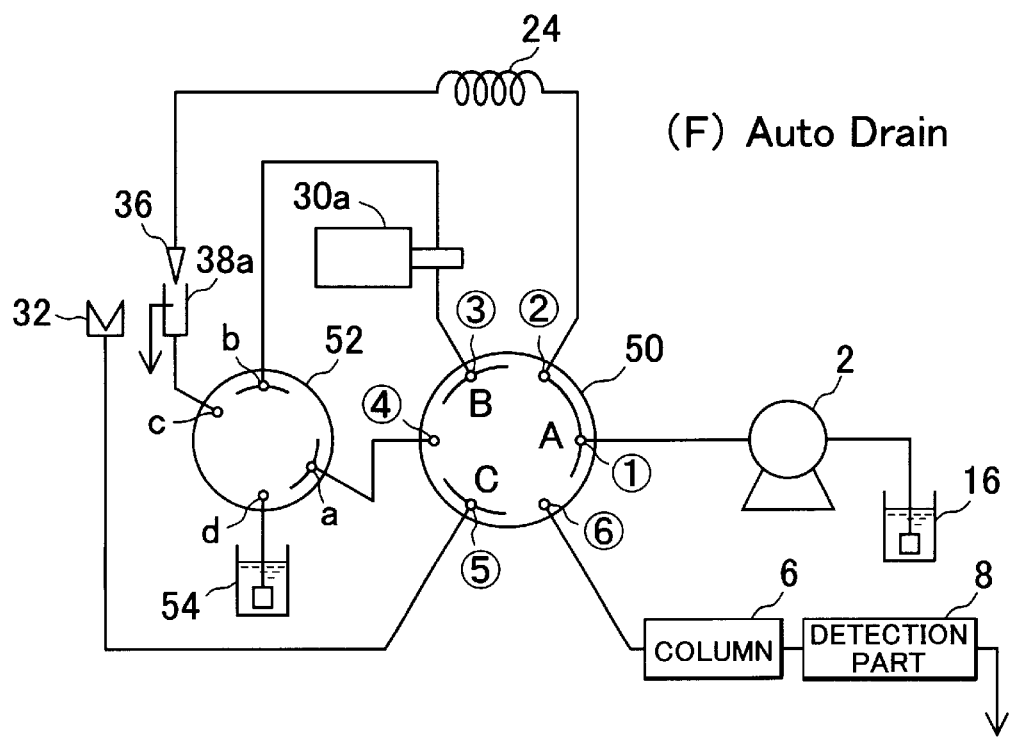
FIG. 9 is a schematic channel block diagram showing the embodiment in an Auto Drain position.

A stator of the low pressure valve 52 has four ports "a" to "d", while its rotor has channel grooves capable of taking three positions including a position for connecting the ports "b" and "c", a position for connecting the ports "d" and "a" as shown in FIG. 7 as described later and a position for connecting no ports as shown in FIG. 9 described later. Thus, the low-pressure valve 52 is also a three-position valve.

The port $\hat{1}$ of the high pressure valve 50 is connected to a channel supplied with a mobile phase stored in a mobile phase container 16 by a pump part 2. A channel connected with the port $\hat{2}$ is provided with a sampling loop 24, and a sampling needle 36 is provided on the forward end of the channel. A channel connected with the port $\hat{3}$ is connected with the port "b" of the low pressure valve 52 through a measuring pump 30a corresponding to the measuring syringe 30 of the embodiment shown in FIG. 2. The port $\hat{4}$ is connected with the port "a" of the low-pressure valve 52. The port $\hat{5}$ is connected with an injection port 32. The port $\hat{6}$ is connected with an analytic channel reaching a detection part 8 through a column 6.

The port "c" of the low-pressure valve 52 is connected with a rinse port 38a having the function of the drain port 38 according to the embodiment shown in FIG. 2. The rinse port 38a, which is supplied with a rinse for rinsing the sampling needle 36, can discharge a mobile phase from the sampling needle 36 to serve as the drain port. The rinse and the mobile phase overflow the rinse port 38a to be discharged into a drain. A channel connected with the port "d" is guided to a rinse 54.

FIGS. 4 to 8 show sampling operations in order of positions.

FIG. 4 shows a Ready (analyzing) position (A), where the ports $\hat{1}$ and $\hat{2}$ and the ports $\hat{5}$ and $\hat{6}$ are connected in the high pressure valve 50 so that the mobile phase fed by the pump part 2 passes through the sampling loop 24 and flows through a channel connecting the column 6 and the detection part 8 through a connection point between the sampling needle 36 and the injection port 32.

The ports "b" and "c" are connected in the low-pressure valve 52, and the measuring pump 30a is open to the atmosphere through the rinse port 38a.

Figure 5:
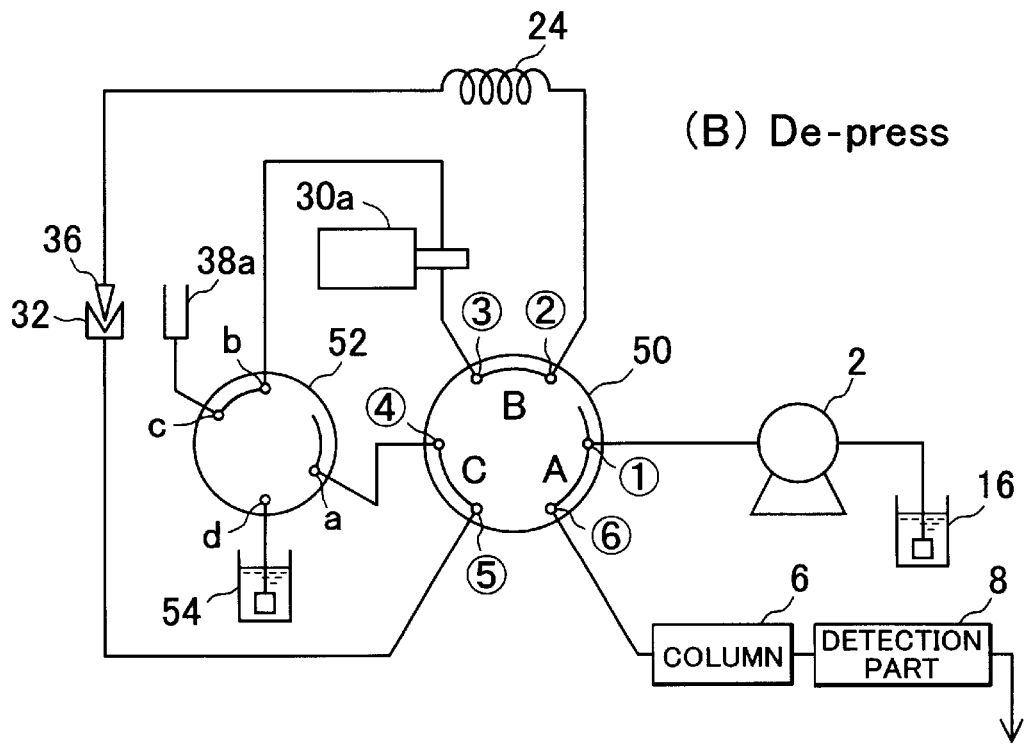
FIG. 5 is a schematic channel block diagram showing the embodiment in a De-press position.

FIG. 5 shows a De-press (depressurization step) position (B), where the high pressure valve 50 is switched to connect the ports $\hat{2}$ and $\hat{3}$, thereby opening a channel including the sampling loop 24 to the atmosphere through the measuring pump 30a and the rinse port 38a. Further, the ports $\hat{1}$ and $\hat{6}$ of the high pressure valve 50 are so connected that the mobile phase continuously flows through the channel connecting the column 6 and the detection part 8.

Figure 6:
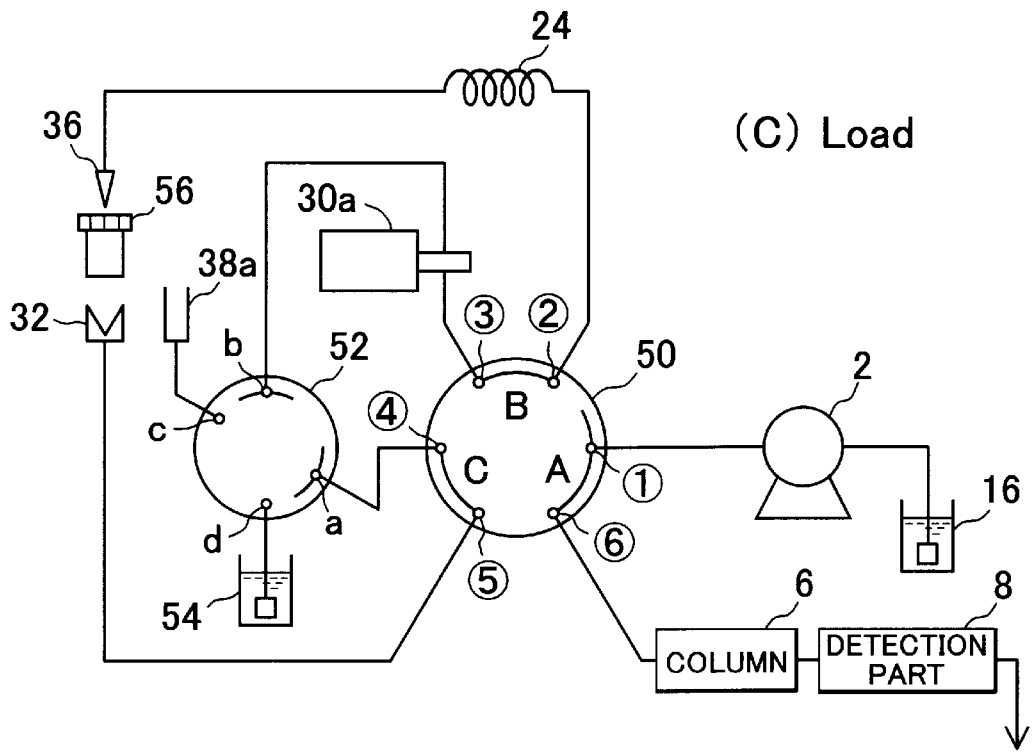
FIG. 6 is a schematic channel block diagram showing the embodiment in a Load position.

FIG. 6 shows a Load (sample suction) position (C), where the low-pressure valve 52 is switched to close the port "b" communicating with the measuring pump 30a. The sampling needle 36 is dipped in a sample vial 56 storing a sample, and the measuring pump 30a is driven to suck and collect the sample into the sampling loop 24.

FIG. 7 shows an INJ/Purge in (sample injection/measuring pump purging) position (D), where the high pressure valve 50 is switched to connect the ports $\hat{1}$ and $\hat{2}$ and the ports $\hat{5}$ and $\hat{6}$ and the sampling needle 36 is returned to the injection port 32. Thus, the mobile phase passes through the sampling loop 24, flows through the channel connecting the column 6 and the detection part 8 through the connection point between the sampling needle 36 and the injection port 32, for introducing the sample collected by the sampling loop 24 to the column 6, which in turn starts separating the sample.

On the other hand, the ports $\hat{3}$ and $\hat{4}$ of the high pressure valve 50 as well as the ports "a" and "d" of the low pressure valve 52 are connected thereby sucking the rinse 54 into the measuring pump 30a for rinsing the channel of the measuring pump 30a.

Figure 8:
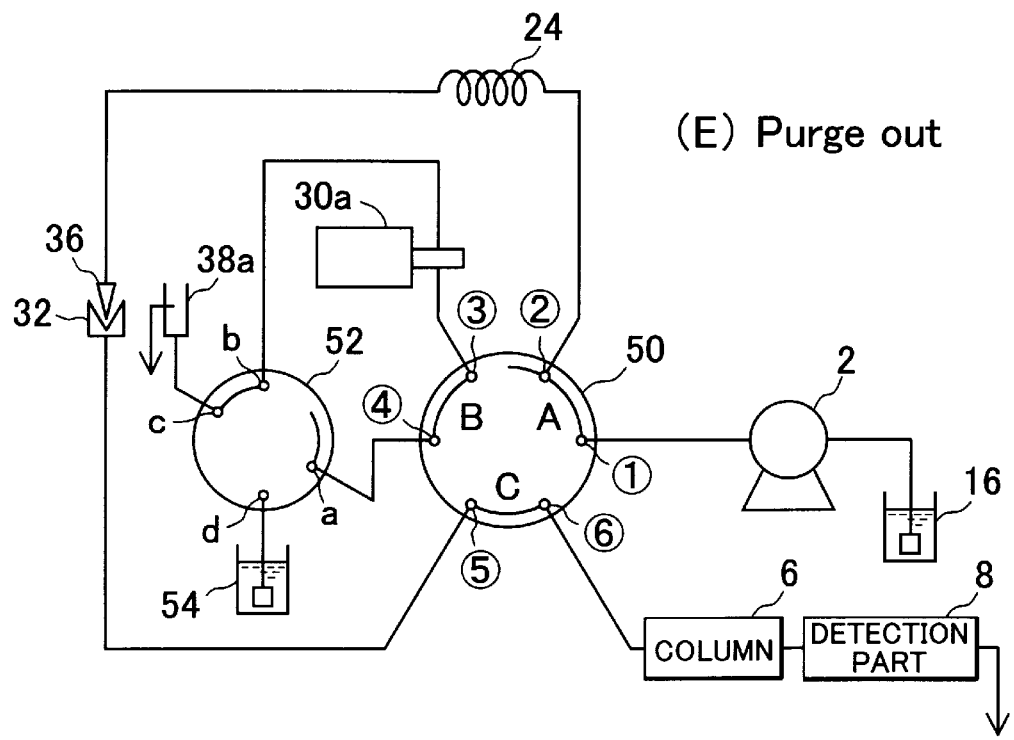
FIG. 8 is a schematic channel block diagram showing the embodiment in a Purge out position.

FIG. 8 shows a Purge out (measuring pump purging) position (E), where the low pressure valve 52 is switched to connect the ports "b" and "c" while closing the port "a". The measuring pump 30a is driven to discharge the rinse 50 sucked therein from the rinse port 38a. The high-pressure valve 50 is left intact to continue analysis, and the detection part 8 detects sample components separated in the column 6.

Thus, the sample is automatically collected in the sampling loop 24, injected into the column 6, separated and analyzed successively through the positions (A)→(B)→(C)→(D)→(E)→as shown in FIGS. 4 to 8.

FIG. 9 shows an Auto Drain (automatic discharge) position (F) in this embodiment. In this position, only the ports $\hat{1}$ and $\hat{2}$ of the high pressure valve 50 are connected and the sampling needle 36 is moved toward the rinse port 38a. The remaining ports of the high-pressure valve 50 and all ports of the low-pressure valve 52 are closed. The mobile phase is fed by the pump part 2, and discharged in the rinse port 38a through the high-pressure valve 50 and the sampling loop 24.

An operation of filling up the overall channels with the mobile phase or substituting the mobile phase in the Auto Drain position (F) shall now be described.

Switching of the high pressure valve 50 and the low pressure valve 52 and movement of the sampling needle 36 are controlled through the Ready position (A)→the De-press position (B)→the Auto Drain position (F)→the De-press position (B)→the Ready position (A).

First, the chromatograph is in the Ready position (A) shown in FIG. 4.

Then, the position is switched to the Auto Drain position (F) shown in FIG. 9 through the De-press position (B) shown in FIG. 5. In the Auto Drain position (F), the pump part 2 is switched to high-speed driving, and the mobile phase is filled up or substituted in a short time. Thereafter the position is returned to the Ready position (A) through the De-press position (B).

A control part 40 (not shown) similar to that shown in FIG. 2 controls the analysis and the operation of filling up with or substituting the mobile phase according to this embodiment.

Although the present invention has been described and illustrated in detail, it is clearly understood that the same is by way of illustration and example only and is not to be taken by way of limitation, as the spirit and scope of the present invention is limited only by the terms of the appended claims.

What is claimed is:

1. A liquid chromatograph comprising a column separating a sample, a feed part feeding a mobile phase to said column, a sample introduction part collecting said sample from a sampling needle into a sampling loop and introducing said collected sample into a mobile phase channel upstream said column by switching a channel switching valve, a detection part detecting said sample separated in said column and a control part controlling the operations of said feed part and said sample introduction part, said liquid chromatograph further comprising:

a drain port discharging a liquid discharged from said sampling needle outward, wherein said control part switches said channel switching valve for connecting said feed part to a channel connecting said sampling needle through said sampling loop, locates said sampling needle on said drain port, and controls an operation switching said feed part to high-speed driving in addition to said control.

2. The liquid chromatograph in accordance with claim 1, wherein said feed part has no outlet for directly discharging said mobile phase outward.

3. The liquid chromatograph in accordance with claim 1, wherein said channel switching valve of said sample introduction part is a two-position valve switched between a position for connecting said feed part to said column through said sampling loop and a position for directly connecting said feed part to said column, and channel connection is so performed that a measuring member for collecting said sample is connected to said sampling loop on said position for directly connecting said feed part to said column.

4. The liquid chromatograph in accordance with claim 1, wherein said channel switching valve of said sample introduction part is a three-position valve switched among a position for connecting said feed part to said column through said sampling loop, a position for directly connecting said feed part to said column and a position for connecting said feed part to said sampling loop and closing an upstream part of said column, and channel connection is so performed that a measuring member for collecting said sample is connected to said sampling loop on said position for directly connecting said feed part to said column.

5. The liquid chromatograph in accordance with claim 1, wherein a plurality of mobile phase containers storing different mobile phases are connected to a suction side of said feed part through electromagnetic valves respectively so that said mobile phases can be selected by opening/closing said electromagnetic valves.

* * * * *